United States Patent
Kidooka

(10) Patent No.: US 7,326,209 B2
(45) Date of Patent: Feb. 5, 2008

(54) BIPOLAR HIGH FREQUENCY TREATMENT TOOL FOR ENDOSCOPE

(75) Inventor: Satoshi Kidooka, Tokyo (JP)

(73) Assignee: PENTAX Corporation, Tokyo (JP)

( * ) Notice: Subject to any disclaimer, the term of this patent is extended or adjusted under 35 U.S.C. 154(b) by 94 days.

(21) Appl. No.: 10/619,563

(22) Filed: Jul. 16, 2003

(65) Prior Publication Data

US 2004/0019352 A1    Jan. 29, 2004

(30) Foreign Application Priority Data

Jul. 29, 2002  (JP) .............................. 2002-219380

(51) Int. Cl.
*A61B 18/18* (2006.01)

(52) U.S. Cl. ......................... 606/51; 606/205

(58) Field of Classification Search ............ 606/45–52, 606/205–207; 600/562–567
See application file for complete search history.

(56) References Cited

U.S. PATENT DOCUMENTS

| | | | | |
|---|---|---|---|---|
| 5,035,696 A | * | 7/1991 | Rydell .......................... 606/47 |
| 5,258,006 A | * | 11/1993 | Rydell et al. ................ 606/205 |
| 5,323,768 A | | 6/1994 | Saito et al. |
| 5,482,054 A | * | 1/1996 | Slater et al. ................ 600/564 |
| 5,536,248 A | * | 7/1996 | Weaver et al. .............. 604/506 |
| 5,603,711 A | * | 2/1997 | Parins et al. ................. 606/51 |
| 5,697,949 A | * | 12/1997 | Giurtino et al. ............ 606/205 |
| 5,743,906 A | * | 4/1998 | Parins et al. .................. 606/51 |
| 5,762,613 A | * | 6/1998 | Sutton et al. ................ 600/564 |
| 5,820,630 A | * | 10/1998 | Lind .......................... 606/208 |
| 5,827,278 A | * | 10/1998 | Webster, Jr. ................. 606/41 |
| 5,908,437 A | * | 6/1999 | Asano et al. ................ 606/205 |
| 6,767,349 B2 | * | 7/2004 | Ouchi .......................... 606/51 |
| 2002/0123667 A1 | | 9/2002 | Ouchi |
| 2003/0191465 A1 | * | 10/2003 | Yahagi et al. ................. 606/48 |

FOREIGN PATENT DOCUMENTS

| | | |
|---|---|---|
| JP | 2528223 | 6/1996 |
| JP | 10-165359 | 6/1998 |
| JP | 11-113918 | 4/1999 |
| JP | 11-342135 | 12/1999 |
| JP | 2000-139942 | 5/2000 |
| JP | 3086166 | 7/2000 |
| JP | 2000-271128 | 10/2000 |
| JP | 2002-253570 | 9/2002 |

* cited by examiner

*Primary Examiner*—Michael Peffley
(74) *Attorney, Agent, or Firm*—Greenblum & Bernstein, P.L.C.

(57) ABSTRACT

A bipolar high frequency treatment tool includes a flexible insulating tube to be inserted through an accessory channel of the endoscope. The insulating tube has a pair of guide channels extending over the length thereof through which a pair of conductive wires is passed. An end effector is attached to a distal end of the insulating tube. The end effector includes a pair of electrodes that opens and closes like a pair of pincers. The pair of electrodes is connected with the pair of wires so that a high frequency power can be supplied to the pair of electrodes.

15 Claims, 4 Drawing Sheets

BIPOLAR HIGH FREQUENCY TREATMENT TOOL FOR ENDOSCOPE

BACKGROUND OF THE INVENTION

The present invention relates to a bipolar high frequency treatment tool that is to be inserted into a human body through an accessory channel of an endoscope.

A typical bipolar high frequency treatment tool is disclosed, for example, in Japanese Patent Application Provisional Publication No. P2000-271128. The treatment tool disclosed in the above-mentioned publication has a pair of electrodes mounted to a distal end of a flexible sheath so as to open and close like a pair of pincers.

The pair of electrodes is coupled to a pair of wires to be remotely operated, or opened and closed, from the proximal end of the treatment tool by advancing/retracting the wires within the sheath. The wires are also utilized to supply high frequency power to the electrodes. That is, the wires are arranged to connect one of the electrodes with a positive pole of a high frequency power supply while the other one with a negative pole.

In order to prevent short circuits between the wires placed side by side in the sheath, the wires are covered with insulating layers or covers. The insulating layers of the wires, however, cannot be made thick since the overall diameter of the wire is restricted to a small amount due to the small inner diameter of the sheath. Thus, sufficient insulation between wires could not be achieved when a large amount of high frequency voltage is applied between the wires.

Therefore, there is a need for a bipolar high frequency treatment tool for an endoscope in which wires supplying high frequency power to an end effector is sufficiently insulated from each other.

SUMMARY OF THE INVENTION

The present invention is advantageous in that a bipolar high frequency treatment tool for an endoscope that satisfies the above mentioned need is provided.

According to an aspect of the invention, the bipolar high frequency treatment tool includes a flexible insulating tube to be inserted through an accessory channel of the endoscope. The insulating tube is made of polytetra-fluoro-ethylene or silicone resin, for example, and is provided with a pair of guide channels extending over the length thereof. An end effector is attached to a distal end of the insulating tube. A pair of conductive wires are passed through different one of the pair of guide channels and coupled to the end effector to provide high frequency power to the end effector.

In the bipolar high frequency treatment tool configured as above, the conductive wires are well insulated from each other within the insulation tube since the wires are passed through different one of the pair of guide channels. Accordingly, it is not necessary to cover each wire with a thick insulation layer. Even a pair of naked wire can be utilized as the conductive wires which reduces the total cost of the bipolar high frequency treatment tool.

Optionally, the guide channels are arranged symmetric with respect to a longitudinal center axis of the insulating tube.

Optionally, the bipolar high frequency treatment tool may further include an operating portion connected to a proximal end of the insulating tube, which operating portion advances and retracts the pair of conductive wires within the guide channels to operate the end effector. In this case, the conductive wires not only serve as power supply lines but also as lines for transmitting mechanical force for driving the end effectors.

In the above case, each of the guide channels may be formed to have an inner diameter slightly larger than an outer diameter of the conductive wire so that the conductive wire can smoothly slide within each guide channel as being pushed or pulled by the operating portion.

In some embodiments of the invention, the end effector includes a pair of electrodes pivotably supported at the distal end of the insulating tube so as to open and close like a pair of pincers, and each of the pair of electrodes is coupled to different one of the pair of conductive wires.

In the above case, the bipolar high frequency treatment tool may further include a clevis attached to the distal end of the insulating tube, a pair of pins, such as metal pins, supported by the clevis so as to be spaced apart from each other and cross a slit of the clevis. Each of the pair of electrodes may be pivotably mounted on different one of the pair of pins. Optionally, an insulating spacer may be placed between the electrodes so as to be supported by the pair of pins to ensure insulation between the electrodes within the slit of the clevis.

BRIEF DESCRIPTION OF THE ACCOMPANYING DRAWINGS

FIG. 1 schematically shows a bipolar high frequency treatment tool according to an embodiment of the invention connected to a high frequency power supply;

DETAILED DESCRIPTION OF THE EMBODIMENTS

Hereinafter, an embodiment of the invention will be described with reference to the accompanying drawings.

Figure 1:
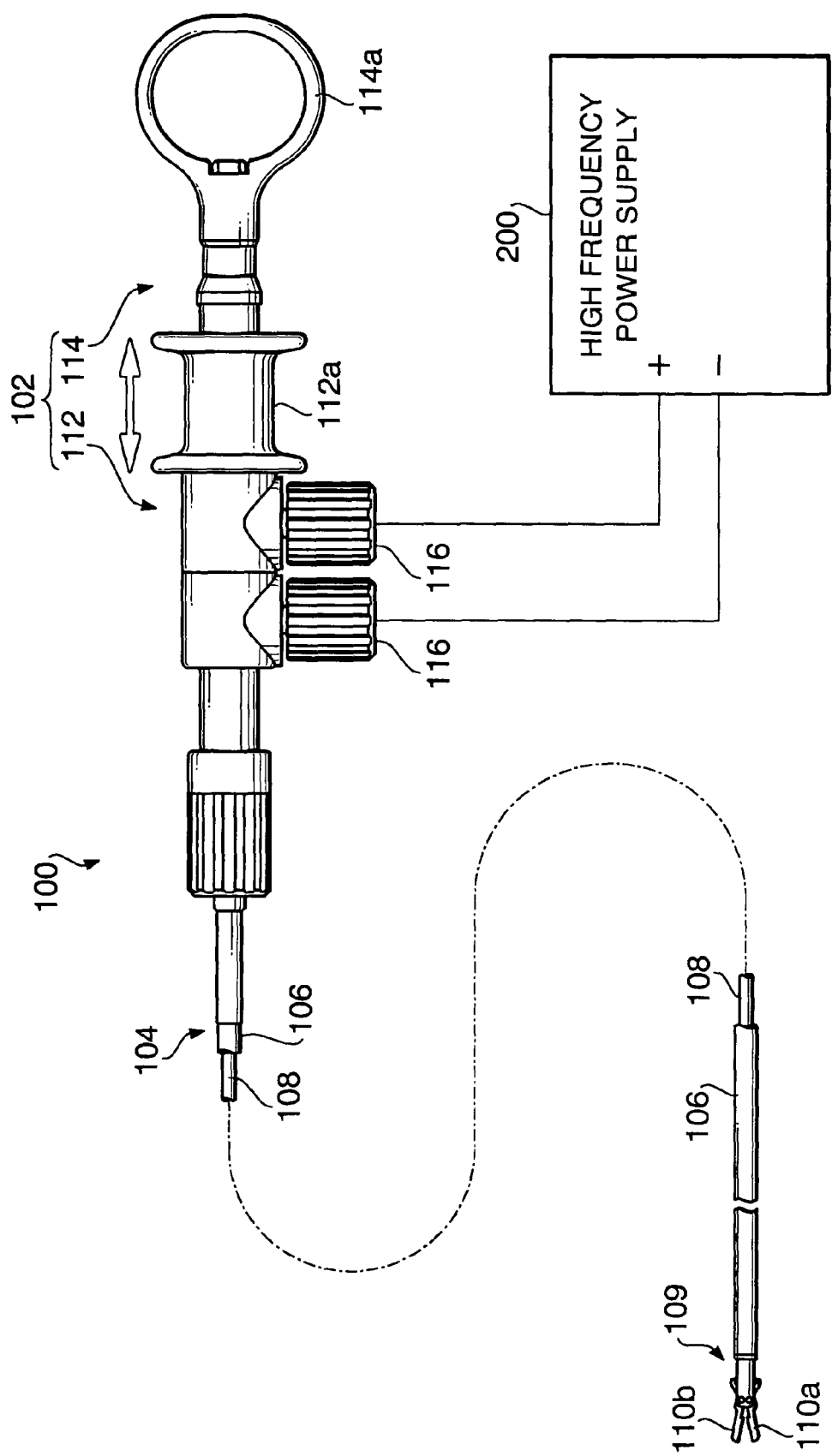

FIG. 1 schematically shows a bipolar high frequency treatment tool 100 according to an embodiment of the invention connected to a high frequency power supply 200.

The treatment tool 100 includes an operating portion 102 and an inserting portion 104 connected to the distal end of the operating portion 102.

The inserting portion 104 is provided in a form and size that allows it to be introduced into a body cavity through an accessory channel of an endoscope (not shown). The inserting portion 104 includes an elongated and flexible tube 106, and a pair of conductive wires 108 (only one is shown) slidably passed through the tube 106. The tube 106 is made of insulating material such as poly-tetrafluoro-ethylene (PTFE) or silicone resin. In an exemplary embodiment, the tube 106 is about 1 m to 2 m long and has an outer diameter of about 2 mm to 3 mm.

An electrode assembly 109 is mounted to the distal end of the inserting portion 104. The electrode assembly 109 includes an end effector, or a pair of electrodes 110 that are connected to the conductive wires 108.

The operating portion 102 includes a cylindrical portion 112 and a rod portion 114 slidably inserted into the cylindrical portion 112.

The cylindrical portion 112 has a circumferential groove 112a at a proximal end thereof. A user of the treatment tool 100 can hold the operating portion 112 by pinching it at the groove 112a with his index finger and long finger.

The rod portion 114 has a ring 114a into which the user can insert his thumb to slide the rod portion 114 within the cylindrical portion 112 back and forth.

The rod portion 114 is connected with the pair of wires 108 in the cylindrical portion 112 such that the wires 108 retract and advance within the tube 106 as the rod portion 114 is moved back and forth with respect to the cylindrical portion 112.

The conductive wires 108 are detachably connected to power supply lines of the high frequency power supply 200 via a pair of connectors 116 provided to the side surface of the cylindrical portion 112. One of the conductive wires 108 is connected to the positive terminal of the power supply 200 and the other to the negative terminal.

Figure 2:
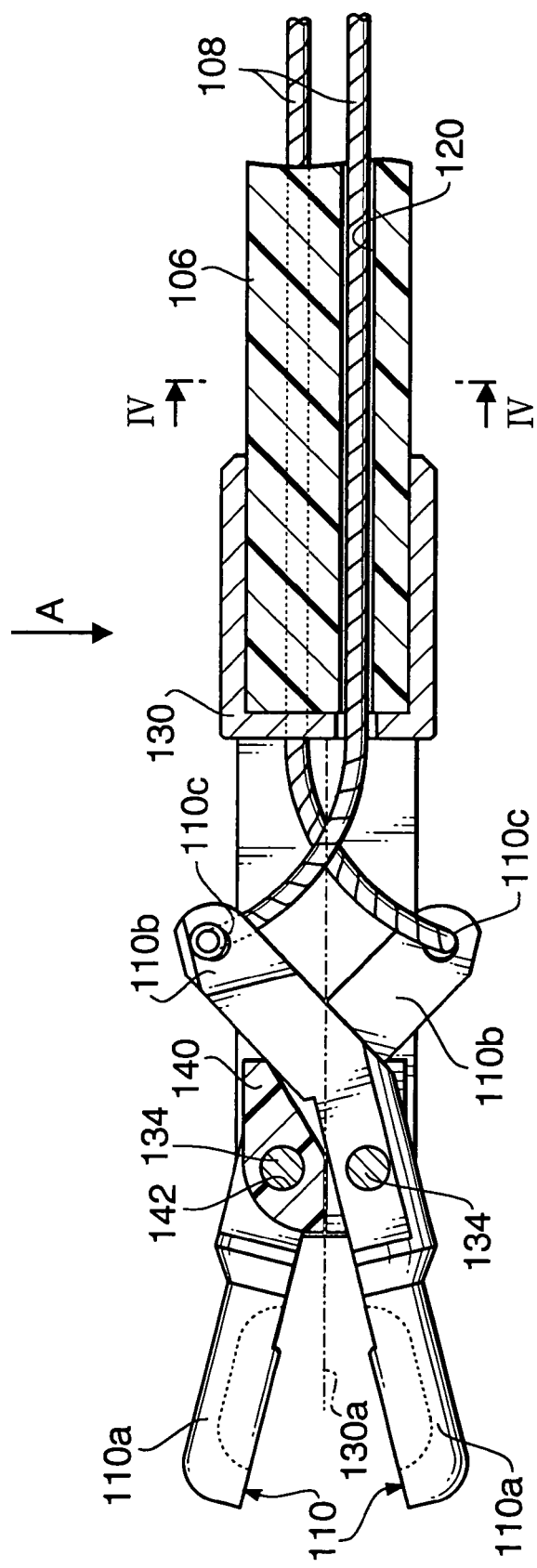
FIG. 2 is sectional side view of the distal end of the treatment tool shown in FIG. 1.
Figure 3:
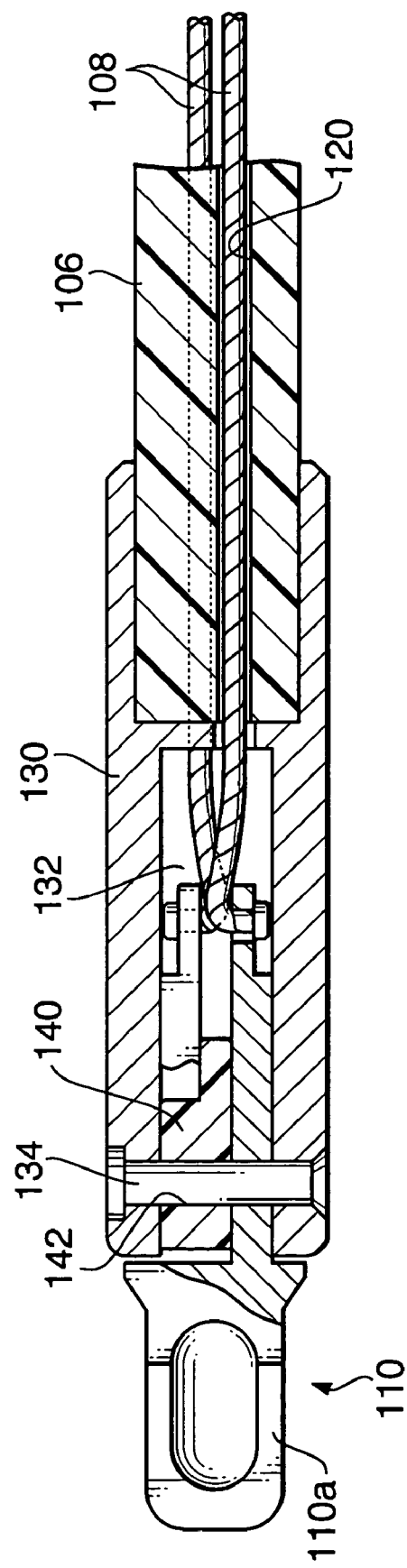
FIG. 3 is a sectional view of the distal end of the treatment tool observed from the direction indicated by the arrow A in FIG. 2.
Figure 4:
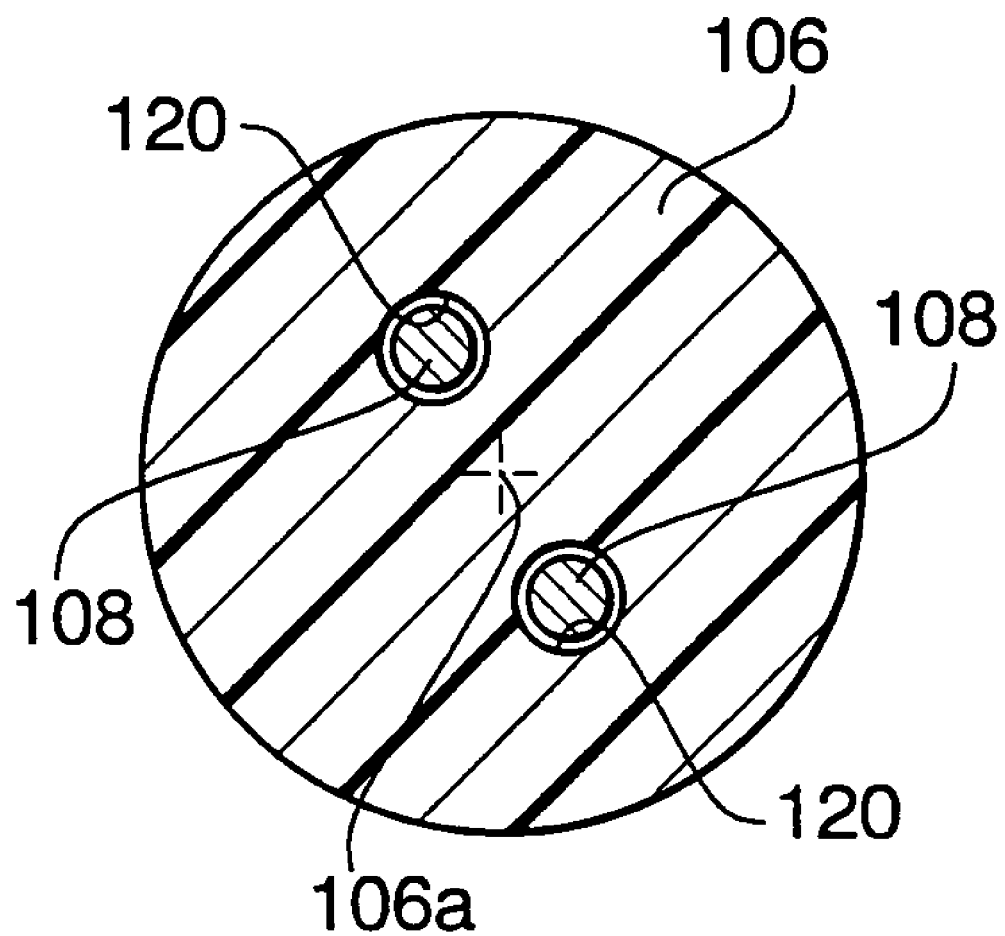
FIG. 4 is a sectional view of the inserting portion of the treatment tool taken along a line IV-IV in FIG. 2.

FIG. 2 is sectional side view of the distal end of the treatment tool 100 shown in FIG. 1, and FIG. 3 is a sectional view of the distal end of the treatment tool 100 observed from the direction indicated by the arrow A in FIG. 2. FIG. 4 is a sectional view of the inserting portion 104 of the treatment tool 100 taken along a line IV-IV in FIG. 2. Note that FIGS. 2 and 3 are drawn as a composite view combining cross sectional views at various positions.

As mentioned previously, the tube 106 is an elongated and flexible tube made of insulating material. As shown in FIG. 4, the tube 106 is provided with a pair of guide channels 120 extending over the length of the tube 106. The wires 108 are passed through respective ones of the pair of guide channels 120 from the proximal end of the tube 106 to the distal end. Thus, the wires 108 are isolated from each other in the tube 106.

The guide channels 120 are formed symmetrically with respect to the longitudinal center axis 106a of the tube 106 and spaced apart from each other for about 0.5 mm. This arrangement ensures good insulation between the wires 106.

The conductive wires 106 are naked twisted stainless steel wires, that is, the wires are not covered with any layers including insulating layers. The use of such naked wires allows cost reduction of the treatment tool 100.

The guide channels 120 of the tube 106 are formed to have inner diameters slightly larger than the outer diameters of the wires 106 so that the wires can smoothly slide within respective guide channels. The guide channels, however, are formed to have an inner diameter small enough to prevent the wires therein from buckling or folding within the guide channels as the wires are advanced and retracted within the guide channels 120. In the present embodiment, the inner diameter of each guide channel 120 is about 0.1 to 0.3 mm larger than the outer diameter of each wire 106.

Referring to FIGS. 2 and 3, a supporting member (clevis) 130 is attached to the distal end of the tube 106. The supporting member is made of insulating material such as rigid plastic or ceramic, and is provided with a slit 132 having a constant width.

A pair of metal (stainless steel) pins 134 is fixed to the distal portion of the supporting member 130 so as to cross the slit 132. The pins 134 are arranged spaced apart from each other and also parallel to each other. The pins 134 are also arranged such that a center axis 130a of the supporting member 130 passes through between the pins 134.

The pair of elongated electrodes 110 is pivotably mounted on the pair of pins 134 so as to open and close like a pair of pincers. Each electrode 110 is mounted on a different one of the pins 134 to avoid making a short circuit through the pins 134.

The distal portion 110a of each electrode 110 is placed outside the slit 132 and formed into a cup like shape. When the pair of electrodes 110 is closed, the electrodes come into contact to each other only at the cup like portions 110a with the concave sides thereof facing to each other.

It should be noted, however, that the shape of the distal portion 110a of each electrode 110 is not limited to above-mentioned one. The distal portion of each electrode 110 may be also formed into a rod like shape or any other shape.

An insulating spacer 140 is placed in the slit 132 of the supporting member 130 between the pair of electrodes 110 so as to electrically isolate the electrodes from each other within the slit 132. The spacer 140 has a pair of through holes 142 (only one is shown in FIGS. 3 and 4) and is supported by the pins 134 passed through respective through holes 142.

A through hole 110c is formed in a vicinity of the proximal end of each electrode 110. The tip end of each wire 106 is passed through the through hole 110c of the corresponding electrode 110 to be coupled therewith.

The proximal portion 110b of each electrode 110 is slightly bent so that each electrode 110 easily rotate about the corresponding pin 134 when the corresponding wire 108 is advanced/retracted along the guide channel 120 of the tube 106 by manipulating the operating portion 102.

The inserting portion 104 of treatment tool 100 configured as above is introduced into a body cavity such as a stomach through an endoscope and the electrodes 110 are located in the vicinity of a target portion of the mucosa.

Then, the operating portion 102 of the treatment tool 100 is operated such that the pair of conductive wires 108 is slid forwards within the sheath 106 and swing the electrodes 110 to the open position. Then, the electrodes 110 are moved by the endoscope such that the target portion of the mucosa is located between the electrodes 110.

Next, the pair of conductive wires 108 are retracted by pulling back the rod portion 114 with respect to the cylindrical portion 112 to move the electrodes 110 to the closed position and thereby grasping the target mucosa.

Next, a high frequency electrical power is supplied from the power supply 200 to the electrodes 110 via the conductive wires 108. As a result, a high frequency current flows through the mucosa placed between the electrodes 110 and coagulates the mucosa.

The present disclosure relates to the subject matter contained in Japanese Patent Application No. P2002-219380, filed on Jul. 29, 2002, which is expressly incorporated herein by reference in its entirety.

What is claimed is:

1. A bipolar high frequency treatment tool for an endoscope, comprising:
    a flexible insulating tube configured to be inserted through an accessory channel of the endoscope, said insulating tube having a pair of generally circular guide channels extending over a length of the insulating tube, said guide channels are arranged symmetric with respect to a longitudinal center axis of said insulating tube and spaced from each other by about 0.5 mm;
    a pair of electrodes pivotably supported at the distal end of said insulating tube so as to open and close like a pair of pincers; and
    a pair of conductive wires, each wire passed through a different one of said pair of guide channels and coupled to a respective electrode of said pair of electrodes to provide high frequency power to said pair of electrodes, the pair of conductive wires being naked twisted stainless steel wires, wherein:

each of said guide channels has an inner diameter slightly larger than an outer diameter of said conductive wire; and a plane defined by said pair of conductive wires is different from a plane defined by opening and closing motion of said pair of electrodes.

2. The bipolar high frequency treatment tool according to claim 1, wherein said insulating tube is made of poly-tetra-fluoro-ethylene.

3. The bipolar high frequency treatment tool according to claim 1, wherein said insulating tube is made of silicone resin.

4. The bipolar high frequency treatment tool according to claim 1, further comprising an operating portion connected to a proximal end of said insulating tube, said operating portion advancing and retracting said pair of conductive wires within said guide channels to operate said pair of electrodes.

5. The bipolar high frequency treatment tool according to claim 1, further comprising;

a clevis attached to the distal end of said insulating tube;

a pair of pins supported by said clevis and positioned such that axes of the pins are spaced apart from each other, each of the pins being configured to extend across a slit of said clevis, and an insulating spacer supported by said pair of pins between said pair of electrodes;

wherein each of said pair of electrodes is pivotably mounted on a different one of said pair of pins.

6. The bipolar high frequency treatment tool according to claim 5, wherein said pair of pins are made of metal.

7. The bipolar high frequency treatment tool according to claim 1, said guide channels being configured to have an inner diameter sized to prevent the wires received therein from deforming as the wires are advanced and retracted within the guide channels.

8. The bipolar high frequency treatment tool according to claim 1, wherein said pair of conductive wires cross each other in the region where they are coupled to said pair of electrodes.

9. A bipolar high frequency treatment tool for an endoscope, comprising:

a flexible insulating tube configured to be inserted through a channel of the endoscope, said insulating tube having a pair of guide channels extending over a length of said insulating tube and being spaced from each other by about 0.5 mm;

a pair of electrodes pivotably supported at the distal end of said insulating tube so as to open and close each of said pair of electrodes;

a pair of conductive wires, each wire passed through a different one of said pair of guide channels and coupled to a respective electrode of said pair of electrodes to provide high frequency power to said pair of electrodes, each wire being an uninsulated twisted stainless steel wire, wherein:

each of said guide channels has an inner diameter slightly larger than an outer diameter of said conductive wire; and a plane defined by said pair of conductive wires is different from a plane defined by opening and closing motion of said pair of electrodes.

10. The bipolar high frequency treatment tool according to claim 9, wherein said insulating tube comprises poly-tetra-fluoro-ethylene.

11. The bipolar high frequency treatment tool according to claim 9, wherein said insulating tube comprises silicone resin.

12. The bipolar high frequency treatment tool according to claim 9, wherein said guide channels are symmetric with respect to a longitudinal center axis of said insulating tube.

13. The bipolar high frequency treatment tool according to claim 9, further comprising an operator connected to a proximal end of said insulating tube, said operator configured to advance and retract said pair of conductive wires within said guide channels to operate said pair of electrodes.

14. The bipolar high frequency treatment tool according to claim 9, wherein the guide channels are configured to have an inner diameter sized to prevent the wires received therein from deforming as the wires are advanced and retracted within the guide channels.

15. The bipolar high frequency treatment tool according to claim 9, wherein said pair of conductive wires cross each other in the region where they are coupled to said pair of electrodes.

* * * * *